United States Patent [19]

Froggatt

[11] 4,132,895

[45] Jan. 2, 1979

[54] RADIOGRAPHY

[75] Inventor: Robert J. Froggatt, Southall, England

[73] Assignee: EMI Limited, Hayes, United Kingdom

[21] Appl. No.: 819,577

[22] Filed: Jul. 27, 1977

[30] Foreign Application Priority Data

Aug. 28, 1976 [GB] United Kingdom ............... 35912/76

[51] Int. Cl.² ............................................. A61B 6/02
[52] U.S. Cl. ................................ 250/445 T; 250/505
[58] Field of Search ........................... 250/445 T, 505

[56] References Cited

U.S. PATENT DOCUMENTS 3,866,047  2/1975  Hounsfield ................... 250/445 T Primary Examiner—Alfred E. Smith
Assistant Examiner—T. N. Grigsby
Attorney, Agent, or Firm—Cooper, Dunham, Clark, Griffin & Moran

[57] ABSTRACT

In a computerized tomographic CT scanner, a lateral scan of a pencil beam of radiation is effected by causing an apertured, annular collar to rotate around a source of a fan-shaped spread of radiation. The motion of the collimator causes a pencil like beam to sweep angularly across the body. Successive sweeps, caused by successive apertures, are in the same direction.

7 Claims, 1 Drawing Figure

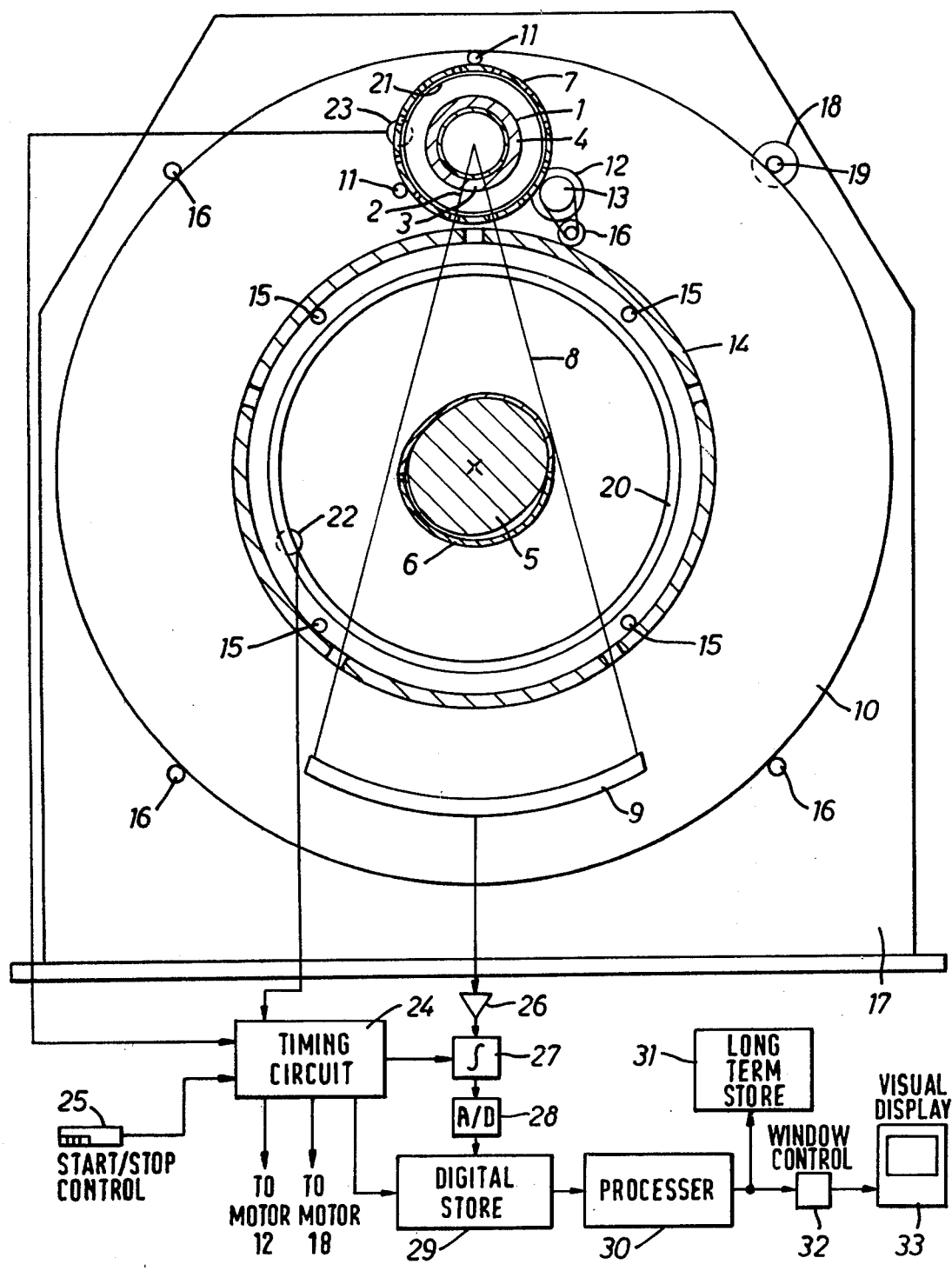

RADIOGRAPHY

The present invention relates to radiography and it relates more especially to that branch of radiography which has become known as computerised axial tomography, or briefly C.A.T. Apparatus for performing C.A.T. is described and claimed in U.S. Pat. No. 3,778,614 and has the object of producing a representation of the variation of penetrating radiation with position over a slice disposed cross-sectionally of a body under examination. Such representations have provied useful in diagnosing diseases, of injuries to, the human body and are capable of displaying features which would not be observable in conventional X-ray shadowgraph pictures, because of the masking effect of highly absorbing features such as bones.

It will be observed from the specification of the aforementioned Patent, that, in order to perform C.A.T., it is the practice to project X-radiation through a slice of a body along many beam paths, some of which intersect within the slice, and to detect the amount of X-radiation emergent from the body along each path. By this means the absorption suffered by the radiation on traversing each path can be determined, and the absorption values so determined are processed, in accordance with a compensated layergramming technique, to produce the desired representation. One example of a suitable compensated layergramming technique is disclosed in the aforementioned Patent and another such technique, which is capable of somewhat faster operation, is disclosed in U.S. Pat. No. 3,924,129.

The present invention is concerned with a scanning technique whereby the required absorption values can be conveniently acquired using a relatively simple scanning mechanism.

According to the invention there is provided radiographic apparatus comprising means defining a patient positin, a source of X-radiation arranged to project said radiation through a region of said patient position along at least one beam path, scanning means for moving said source angularly around said patient position to project said radiation through said region along further beam paths, sub-scanning means for sweeping said radiation laterally across said region to project said radiation through said region along more beam paths, detector means being provided for detecting the radiation emergent from the region along each of said paths, and said sub-scanning means including an apertured collar which at least substantially encircles said source, and means for causing relative rotational motion between said collar and said source whereby said radiation is repetitively swept across said region in the same direction; said radiation faning out from said source to an extent sufficient to accommodate said sweeps.

In order that the invention may be clearly understood and readily carried into effect, one embodiment thereof will now be described, by way of example only, with reference to the accompanying drawing, the single FIGURE of which shows in schematic elevational view, radiographic apparatus in accordance with one example of the invention.

Referring now to the drawing, an X-ray tube 1 is arranged to generate a fan-shaped spread 2 of X-radiation, the spread in this example being of angle 30° and emerging through an aperture 3 in a lead shield 4. The radiation is projected towards a region of a patient position, defined by the apparatus, so as to pass through a preselected slice of a body 5 to be examined. The body 5 is supported on a curved platter 6 which itself rests in a curved groove formed in a table (not shown) and can be driven relative thereto in a direction perpendicular to the plane of the paper. A suitable platter, a table arrangement and drive means are disclosed in U.S. Pat. No. 4,034,224.

Surrounding the tube 1 so as to encircle it is a multi-apertured collar 7. The collar 7 in this example contains twelve equally angularly spaced apertures, the number of apertures being related, of course, to the fan angle of the spread 2 of radiation. With the spacing of the apertures of collar 7 as described only a single pencil beam of radiation (such as that shown at 8) is allowed to emerge from the collar at any time to impinge on a detector arrangement 9 which, in this example, comprises a single, elongated detector formed of a tank containing a noble gas, such as xenon, at a pressure of a few atmospheres and suitable electrodes of known kind by means of which electrical signals, indicative of the amount of radiation impinging on the detector, can be derived therefrom.

The components 1, 7 and 9 are mounted on an annular gantry 10; the tube 1 and detector 9 being fixed thereto in known manner and the collar 7 being rotatably mounted in a number of roller bearings 11. The collar 7 is driven by means of an electric motor 12 and a gear wheel 13 which meshes with gear teeth (not shown) formed all around the periphery of ring 7.

Also supported rotatably on the gantry 10 is a multi-apertured collimator ring 14 which is not in the same plane as the collar 7 and the spread 2 of radiation but intersects that plane at the far side of the body from the tube 1. The ring 14 is mounted to the gantry 10 by means of a number of roller bearings 15 and is rotated by means of a gear wheel 16 which is driven, through a suitable gearing, from the motor 12. The ring 14 is provided to reduce the effects of scatter in the body by making the detector 9 sensitive substantially only to radiation emergent from the body along the pencil beam for the time being selected by collar 7. Clearly the collar 7 and ring 14 have to rotate at related rates because as the collar 7 rotates anti-clockwise, thus causing one of its apertures to sweep a pencil beam of radiation from left-to-right across the body 5, it is necessary for an aperture in the ring 14 to follow the movement of that pencil beam. It is also necessary for a second aperture in ring 14 to follow the movement of the pencil beam swept from left-to-right across the body 5 by the next aperture in collar 7. This is accomplished by suitable gearing as aforesaid, between the two rings and by suitable choice of the number of apertures in the two rings. In this example, there are twelve apertures in collar 7 and five apertures in ring 14. The reason for ring 14 being disposed in a different plane from collar 7 is clear from the drawing, as if the two components were in the same plane the part of ring 14 for the time being disposed between the body and the tube 1 would obstruct the radiation.

The gantry 10 itself is supported by a number of bearings 16 on an apertured main frame 17 which remains stationary and is secured to the floor of a building. The gantry 10 is moved angularly relative to the frame 17 by means of an electric motor 18 and a gear wheel 19, driven thereby, which meshes with gear teeth (not shown) formed all around the periphery of the gantry 10.

It is necessary that the progress of the angular movement of gantry and the rotational movement of collar 7 be accurately monitored, and so each member is formed with a respective graticule 20, 21 which co-operates in known manner with respective photocell-and-detector units 22, 23 to produce electrical timing pulses indicative of such progress. The two sets of timing pulses are applied to a main timing circuit 24, which also receives impulse signals from a remotely located START/STOP control 25. Timing circuit 24 provides driving signals for the two electric motors 12 and 18, and also performs other functions with regard to the processing of signals derived from the detector 9. These signals are applied to an amplifier 26 and thence to an integrator circuit 27 which is read and reset periodically under the influence of signals developed by the timing circuit 24 in response to the pulses applied thereto from the units 22 and 23. The signals so integrated are converted to logarithmic form and digitised in a circuit 28 of known kind, and the signals so treated are applied to a digital store 29, again under the control of timing signals from the circuit 24. Once stored, the data can be processed by any convenient compensated layergram technique in a suitable processing circuit 30 to produce the required representation of the variation in absorption of the X-radiation over the slice of interest in the body 5. The representation is applied to a long term store 31, for example a magnetic tape or disc, and also, through a window control circuit 32 of known kind which selects out of the considerable dynamic range of data in the representation (typically a thousand or more discernable levels) a limited range, centred on a preselected level, for application to a visual display such as a cathode ray tube 33. The display on tube 33 can be photographed, if desired.

In operation, the examination is initiated by the actuation by an operator of the START element of control 25. This causes the scan motor to rotate continuously at a steady speed so as to move the gantry 10 and its attachments angularly, at a steady rate around the body 5. Simultaneously the motor 12 is energised to cause the collar 7 and ring 14 to rotate, thereby to cause a pencil beam of the radiation to sweep repetitively from left to right across the body 5. It will be appreciated that the collar 7 and ring 14 and the operating mechanisms therefor can be regarded as a sub-scanning means, and that the sub-scan is effective to sweep the radiation across the body 5 from left to right many times, for example three hundred and sixty times, during a single revolution of the gantry 10 around the body 5. If it is imagined that the collar 7 and ring 14 are stationary, with apertures therein positioned to allow the radiation to be proejcted through the body along a particular beam path, then operation of the scanning motor 18 such as to move the tube 1 angularly around the body causes the radiation to be projected through the body along further beam paths. The operation of the aforementioned sub-scanning means is effective to repetitively sweep the radiation across the body 5, thereby to cause the radiation to be projected through the body along more beam paths. Typically the inter-relationship between the scanning of gantry 10 and the sub-scanning effected by collar 7 and ring 14 and their operating mechanisms is such that the radiation is swept from left to right across the body for each 1° of angular movement of the gantry and the timing arrangements are such that (say) one hundred and eighty discrete signals are derived from the detector 9 during each sweep of the sub-scan.

Other arrangements are possible without departing from the scope of the invention. For example the collimator ring 14 may be omitted and replaced by a fixed array of collimators disposed on the gantry 10 between the body 5 and the detector 9. Alternatively the collimators provided for the reduction of the effects of scatter can be omitted altogether and the scatter can be evaluated and allowed for as described in U.S. patent application Ser. No. 755629 now U.S. Pat. No. 4,081,681.

If desired, the single detector 9 may be replaced by an array of individual detectors of any convenient kind, such as scintillator crystals coupled to optical-electrical converters such as photomultipliers or photodiodes. Also, shaped attenuators can be provided on the gantry 10 between the tube 1 and the body 5 and/or between the body 5 and detector 9 to compensate in part for the considerable fluctuations of intensity of radiation incident on the detector 9 during each sub-scan due to the changing lengths of the various beam paths through the body 5.

It can be advantageous to ensure that, at or adjacent the extremities of the sweeps effected by the sub-scanning means, the pencil beam of radiation is shifted clear of the body so that it provides a reference signal for the detector.

What I claim is:

1. Radiographic apparatus comprising means defining a patient position, a source of X-radiation arranged to project said radiation through a region of said patient position along at least one beam path, scanning means for moving said source angularly around said patient position to project said radiation through said region along further beam paths, sub-scanning means for sweeping said radiation laterally across said region to project said radiation through said region along more beam paths, detector means being provided for detecting the radiation emergent from the region along each of said paths, and said sub-scanning means including an apertured collar which at least substantially encircles said source, and means for causing relative rotational motion between said collar and said source to repetitively sweep said radiation across said region in the same direction; said radiation fanning out from said source to an extent sufficient to accommodate said sweeps.

2. Apparatus according to claim 1 wherein said collar is formed with a plurality of apertures spaced apart to cause a pencil like beam of radiation to repetitively sweep across said region.

3. Apparatus according to claim 2 including a gantry supporting said source, said sub-scanning means and said detector means, said scanning means moving the gantry and the components supported thereby angularly around the patient position.

4. Apparatus according to claim 3 including an apertured collimator ring mounted on said gantry and surrounding said patient position and means for rotating said ring relative to said gantry to run an aperture of said ring across between said patient position and said detector means in synchronism with each of said sweeps and in alignment with said pencil like beam.

5. Apparatus according to claim 4 including driving motor and gearing means for rotating said collar and said ring at related rates and in opposing directions.

6. Apparatus according to claim 4 wherein said ring is inclined with respect to said collar.

7. Apparatus according to claim 2 wherein said detector means comprises a single, elongated detector constituted by a tank containing xenon under pressure and electrodes.

* * * * *